(12) United States Patent
Asaff Torres et al.

(10) Patent No.: US 11,401,535 B2
(45) Date of Patent: Aug. 2, 2022

(54) PROCESS OF PRODUCTION OF VANILLIN WITH IMMOBILIZED MICROORGANISMS

(75) Inventors: Ali Asaff Torres, Hermosillo (MX); Mayra De La Torre Martinez, Hermosillo (MX); Antonino Berrondo Mir, Jiutepec (MX); Roberto Miguel Macias Ochoa, Mexico City (MX)

(73) Assignee: LABORATORIOS MINKAB, S.A. DE C.V., Tlalnepantla (MX)

( * ) Notice: Subject to any disclaimer, the term of this patent is extended or adjusted under 35 U.S.C. 154(b) by 536 days.

(21) Appl. No.: 12/253,943

(22) Filed: Oct. 18, 2008

(65) Prior Publication Data
US 2011/0065156 A1 Mar. 17, 2011

(30) Foreign Application Priority Data
Oct. 2, 2008 (MX) .................... MX/A/2008/12689

(51) Int. Cl.
*C12P 7/24* (2006.01)
(52) U.S. Cl.
CPC ..................................... *C12P 7/24* (2013.01)
(58) Field of Classification Search
USPC ........................................................ 435/132
See application file for complete search history.

(56) References Cited

U.S. PATENT DOCUMENTS 5,866,380 A 2/1999 Lesage-Meessen et al.

FOREIGN PATENT DOCUMENTS

| EP | 885968 A1 | * 12/1998 | |
| EP | 0885968 A1 | * 12/1998 | ........... C12P 7/24 |
| EP | 0885968 A1 | * 12/1998 | ........... C12P 7/24 |
| EP | 0885968 B1 | 2/2006 | |
| EP | 1734128 A1 | 12/2006 | |
| FR | 2647119 | 11/1990 | |
| MX | 178723 A | 7/1995 | |
| WO | 96/34971 A1 | 11/1996 | |

OTHER PUBLICATIONS

El-Naggar et al., "Effect of support materials on antibiotic MSW2000 production by immobilized *Streptomyces violatus*," J. Gen. Appl. Microbiol., vol. 49, pp. 235-243 (2003).*
Official English Translation of FR 2647119 (18 pages).*
Devi et al., "Production of cephamycin C in repeated batch operations from immobilized *Streptomyces clavuligerus*," Process Biochemistry, vol. 36, pp. 225-231 (2000).*
Anderson et al., "The taxonomy of *Streptomyces* and related genera," International Journal of Systematic and Evolutionary Microbiology, vol. 51, pp. 797-814 (2001).*
Official English Translation of Raimbault et al., FR 2647119 (18 pages); of record.*
El-Naggar et al., "Effect of support materials on antibiotic MSW2000 production by immobilized *Streptomyces violatus*," J. Gen. Appl. Microbiol., vol. 49, pp. 235-243 (2003); of record.*
Devi et al., "Production of cephamycin C in repeated batch operations from immobilized *Streptomyces clavuligerus*," Process Biochemistry, vol. 36, pp. 225-231 (2000); of record.*
Anderson et al., "The taxonomy of *Streptomyces* and related genera," International Journal of Systematic and Evolutionary Microbiology, vol. 51, pp. 797-814 (2001) of record.*
Schwarcz (Monkeys, Myths and Molecules: Separating Fact from Fiction in the Science of Everyday Life, 2015; published by ECW press, Toronto Ontario Canada; ISBN 978-1-1-77090-701-0).*
Krishna, C. (Critical Reviews in Biotechnology, vol. 25, pp. 1-30; 2000).*
El-Naggar et al., J. Gen. Appl. Microbiol., vol. 49, pp. 235-243 (2003); of record.*
Official English Translation of Raimbault et al., FR 2647119; Translation date: Sep. 2011 (18 pages); of record.*
Krishna, C. (Critical Reviews in Biotechnology, vol. 25, pp. 1-30; 2000) (of record).*
Jenkins, N.E., et al., "Development of Mass Production Technology for Aerial Conidia for Use as Mycopesticides," Biocontrol News and Information (1998) vol. 19, No. 1, p. 21N-31N (11 p.).
Viniegra-Gonzalez, G., et al., "Adavantages of Fungal Enzyme Production in Solid State over Liquid Fermentation Systems," Biochemical Engineering Journal 13 (2003), pp. 157-167 (11 p.).
Papagianni M., et al., "Submerged and Solid-State Phytase Fermentation by Aspergillus Niger: Effects of Agitation and Medium Viscosity on Phytase Production, Fungal Morphology and Inoculum Performance," Food Technol. Biotechnol. 39(4) pp. 319-326 (2001) (8 p.).
Gomez, S., "Produccion de Invertasa por Aspergillus Niger en Fermentacion Liquida y Fermentacion Solida," Doctrinal Thesis for Universidad Autonoma Metropolitana, Apr. 2, 2001 (134 p.).
Castilho, L.R., et al., "Economic Analysis of Lipase Production by Penicillium Restrictum in Solid-State and Submerged Fermentations," Biochemical Engineering Journal 4 (2000) pp. 239-247 (9 p.).
Mexican Office Action dated Oct. 8, 2010; Mexican Application No. MX/a/2008/012689 (3 p.).

* cited by examiner

*Primary Examiner* — Sharmila G Landau
*Assistant Examiner* — Paul D Pyla
(74) *Attorney, Agent, or Firm* — Conley Rose, P.C.

(57) ABSTRACT

The present invention refers to a cyclic process for the production of vanillin, including (a) adding a solution of ferulic acid or a salt thereof, to a solid structure containing immobilized microorganisms of the Actinomycetales group, (b) incubating the solid structure to carry out the biotransformation process, (c) recovering the solution obtained in step (b), and (d) repeating steps (a) to (c) by feeding a fresh solution of ferulic acid or a salt thereof.

13 Claims, 2 Drawing Sheets

0 hours  18 hours  22 hours

PROCESS OF PRODUCTION OF VANILLIN WITH IMMOBILIZED MICROORGANISMS

TECHNICAL FIELD OF THE INVENTION

The invention refers to a process to produce vanillin through the biotransformation of ferulic acid with immobilized microorganisms via surface culture.

BACKGROUND

Vanillin is a compound broadly used as a flavor for the food industry, as an aroma in the cosmetic industry and as a precursor for the chemical synthesis of drugs for the pharmaceutical industry. Mostly, the vanillin is obtained by a chemical synthesis starting from the guaiacol and the lignin, however, the current tendency is to use products of natural origin in the human food industry. Natural vanillin has historically been obtained by extraction from the vanilla bean, but there are a limited amount of beans and the total production cost is high.

There have been many efforts to obtain vanillin by alternative biological processes which use microorganisms (bacteria, yeasts, and fungi), enzymatic systems, or vegetable cells. In general, these biological processes involve the biotransformation of a correct precursor development for vanillin. Eugenol, isoeugenol, curcumine, some resins, and ferulic acid have been identified as possible precursors. In most cases, the transformation yields are very low and only a few of them are cost effective for production. These processes involve three steps; sterilization of the equipment, a fermentation period to allow for the growth of the microorganisms, and a biotransformation period, in order to convert ferulic acid into vanillin. Unfortunately, all of these processes suffer from the disadvantage of having batches that require the above three steps.

SUMMARY

A biotransformation process to produce vanillin, through the biotransformation of cinnamic acid derivatives or its salts, in a highly efficient manner, by immobilizing microorganisms in solid structure support by surface culture. Since they are immobilized, after biotransformation, the produced vanillin can be extracted leaving the microorganisms behind and ready to start a new biotransformation process and thus, this system acts as a biocatalyzer.

One version of this process involves immobilizing a microorganism from the actinomycetales group in an effective solid support structure. After draining the residual culture broth of the support structure containing the microorganisms, a solution of ferulic acid or its salts, or other derivatives of cinnamic acid or their salts is then added. Next, all components of the system are incubated for a period of time in order to allow for the biotransformation reaction to occur. The resulting biotransformation solution is then collected and the vanillin is recovered.

Since the microorganisms are held captive in the supports, the step of biocatalysis can be repeated up to 15 times before the biocatalytic capacity is lost and/or detachment of the actinomycetes from the support structure occurs which would then require the cleaning of the equipment and the need to start the whole process again.

BRIEF DESCRIPTION OF DRAWINGS

The details of the characteristics of the invention will be understood with reference to the following description, appended claims, and with the drawings that accompany them.

DETAILED DESCRIPTION

Figure 1:
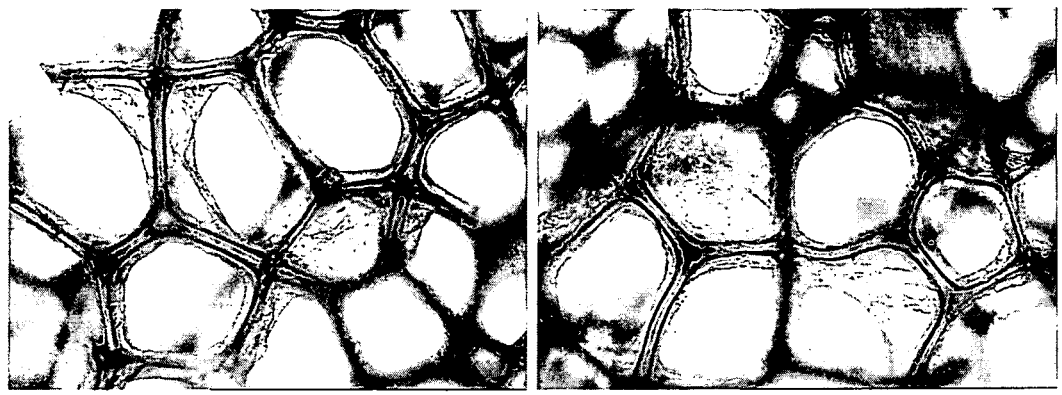
FIG. 1 is a photograph showing *Streptomyces setonii* fixed in the polyurethane foam.

The invention involves a microbiological process with high biotransformation yields of ferulic acid into vanillin. The first part includes the process of adherence of a microorganism of the actinomycetales order, preferably of the *Streptomyces* genera, preferably the *Streptomyces setonii* ATCC 39116 strain, to a solid support structure that has the characteristics of being of one or more pieces of a material which is effectively inert, porous, and absorbent. The adherence of microorganisms occurs through a surface culture that is a simple means of solid-state fermentation which involves a system with the following characteristics: The aqueous culture broth is inoculated with a microorganism, and then is added to a solid support structure, like polyurethane foam, which then absorbs the inoculated aqueous culture broth. In the voids within the foam, the inoculated broth forms very thin films of approximately 0.50 µm to 0.90 µm of thickness. In this manner, a very compact system with a large surface area is obtained, where approximately 1 g of foam containing from 5 ml to 50 ml of broth, and preferably having between 20 ml to 35 ml of broth, allows for a surface culture from 3000 $cm^2$ to 4000 $cm^2$, just as is described in the doctoral thesis of Romero-Gomez, Metropolitan Autonomous University (Iztapalapa campus), Mexico D.F. (2001) and in the Mexican patent MX-178723 for fungal enzyme production and other metabolites. The foam density goes from 0.005 $gml^{-1}$ to 0.070 $gml^{-1}$; the desirable density being 0.015 $gml^{-1}$ to 0.025 $gml^{-1}$, cut in differently shaped support pieces with edges of 0.2 cm to 3.0 cm, and most preferably with edges of 0.4 cm to 0.9 cm, put in closed containers that are either in the form of a flask or a tray, with a height of bed between 1 cm to 10 cm; and preferably from 3 cm to 6 cm to allow an optimal aeration and to avoid the downward seepage of the absorbed liquid due to gravity. Containers with the polyurethane foam that has absorbed the inoculated culture broth, are incubated at 86° F. to 113° F. for a 6 to 35 hour period in which the mycelial growth pattern of the microorganism, which is found on the surface of the films that have formed, allows them to adhere to the support structure, as shown in FIG. 1. At the end of the microorganism growth period, the glucose depletes and the biomass reaches its maximum. The residual nutrients, like the source of nitrogen and salts, in the solution are then separated from the resulting immobilized biomass by squeezing the solid support structure. The waste and other remains are discarded.

For the biotransformation process, a solution of cinnamic acid derivatives or its salts, preferably ferulic acid or its salts, is then added to the solid support structure containing the immobilized microorganisms. The added solution of ferulic acid has a concentration of approximately 5 $gl^{-1}$ to approximately 30 $gl^{-1}$, preferably of approximately 10 $gl^{-1}$ to approximately 20 $gl^{-1}$, with a pH between 7 and 9, preferably between 7.5 to 8.5, with a volume of 5 ml to 50 ml, preferably 20 ml to 30 ml per gram of solid support structure. The biotransformation is carried out at a temperature ranging from 86° F. to 113° F. during a period of 7 to 48 hours. At the molar yield of 70% to 80%. Small quantities of vanillic acid, vanillic alcohol and guaiacol are also resulting byproducts. At the end of this phase, almost all of the ferulic acid has been consumed, and transformed into vanillin which is found in the aqueous films of the surface culture, in concentrations which reach approximately 3 $gl^{-1}$ to approximately 12 $gl^{-1}$, with a suction of the solid support system. All the products of the biotransformation process are recovered in solution by compression, squeezing, squishing, wringing, or centrifugation.

The solid support system with the immobilized microorganisms is now free of liquid, and can now be used for a new biotransformation process after adding a fresh solution of ferulic acid. This process can be repeated cyclically from 3 to 15 times, preferably from 6 to 10 times, with similar biotransformation yields.

It is important to conclude the biotransformation process of the method when the precursor is being depleted because then a degradation of the vanillin formed occurs and vanillic acid and vanillic alcohol are produced. In fact, the biotransformation process involves two different stages; the first has to do with the formation of vanillin and the second with the timing of the degradation of vanillin. It is very important to consider this point in order to facilitate the purification process and assure an effective industrial vanillin yield.

As previously pointed out, this new bioconversion system that we have developed, which involves the use of microorganisms immobilized by surface culture, together with the necessary optimal conditions for the process, allows for the biotransformation of ferulic acid into a high yield of vanillin. Indeed, since the microorganism has been immobilized, our biotransformation system acts as a unique biocatalytic system whose biotransformation cycles can be repeated from 3 up to 15 times, and not having to grow new microorganisms and sterilize the equipment in each batch as is required by other well known submerged culture processes.

The fermentation system is based on the surface culture of a microorganism of the *Streptomyces* genera, preferably, as previously mentioned, of the species *Streptomyces setonii*, preferably of the strain ATCC 39116, in an appropriate culture broth.

To carry out the surface culture an aqueous culture broth is used, which contains salts and the usual nutrients, which is absorbed by an effective solid support structure, like polyurethane foam, among whose internal spaces, thin films are formed. The microorganisms that are formed on the liquid films have a miceliar growth pattern. An adequate culture broth contains a carbon source, a nitrogen source, inorganic salts and growth factors.

Different sugars, preferably, mono or disaccharides, preferably glucose and/or maltose in a concentration of approximately 8 $gl^{-1}$ to approximately 40 $gl^{-1}$, preferably of approximately 15 $gl^{-1}$ to approximately 30 $gl^{-1}$ are used as a source of carbon. Yeast extract, which contains nitrogen growth factors and trace elements, is used in a concentration of approximately 1 $gl^{-1}$ to approximately 15 $gl^{-1}$, preferably in a concentration of approximately 3 $gl^{-1}$ to approximately 10 $gl^{-1}$. Additionally, a magnesium source and a phosphate buffer (of pH 7 to pH 8) are used.

The culture broth is sterilized and then inoculated with a strain of *Streptomyces*. The inoculum comes from the submerged culture of the microorganism in this same culture broth. The inoculum with an age of 15 to 30 hours, preferably between the 18 h to 24 h, is added in a volume of 3% to 6% (v/v). Then, the inoculated broth is added to the sterile-polyurethane foam where it is absorbed, in a volume of 5 ml to 50 ml per gram of foam, preferably of 20 ml to 35 ml per gram of foam, by initiating the growth of the microorganisms via surface culture. The foam containing the inoculated broth is incubated at 86° F. to 113° F., with the growth period having a duration of 6 to 35 hours, preferably from 12 to 24 hours.

Once the growth phase is finished, the polyurethane foam containing the immobilized biomass, is squeezed and compressed in order to drain the residual culture broth. In doing this, the foam again regains its capacity to absorb, and is again fed with a ferulic acid solution with a concentration of approximately 5 $gl^{-1}$ to approximately 30 $gl^{-1}$, preferably of approximately 10 $gl^4$ to approximately 20 $gl^{-1}$, with a pH between 7 and 9, preferably between 7.5 at 8.5. The effective volume of ferulic acid solution is from 5 ml to 50 ml per gram of foam, preferably from 20 ml to 35 ml per gram of foam.

The biotransformation phase begins at the moment of the feeding and has a duration of 7 to 48 hours, preferably from 15 to 28 hours; after this period almost all of the precursor has been consumed and transformed into vanillin and some minor byproducts. Once the biotransformation phase is finished, the foam containing the immobilized biomass is again squeezed and compressed in order to separate the biotransformation solution containing vanillin. The recovered solution carries a small quantity of cellular material that is separated by centrifugation or filtration in order to purify the vanillin. The immobilized microorganisms, in the foam that is free of the biotransformation solution, are again ready to begin a new biotransformation cycle by feeding them a fresh solution of ferulic acid. The system maintains its efficiency and conversion rate from 3 to 15 cycles, preferably 6 to 10 cycles, after which a loss of cellular viability takes place as well as a gradual reduction of the biomass.

It is important to point out that only the phase of development of the microorganisms is performed under sterile conditions, since after the draining of the residual culture broth, the growth of undesirable microorganisms is not possible. Neither during the process of the feeding of the ferulic acid solution nor during the recovery of the vanillin in solution is it possible to contaminate the system. Since both compounds are toxic for most of the microorganisms and only those that have a highly specialized mechanism of disintoxication, like *Streptomyces setonii*, are able to survive.

The technique described in our invention involves the immobilization of an actinomycete in an effective solid support system which allows operating cyclically as a pure biocatalytic method, as well as taking advantage of certain physiological advantages of a certain type of microorganism when they are cultivated by solid fermentation or surface culture. There are many publications which refer to the major physiological and metabolic differences of the microorganisms when they are developed by solid-substrate or submerged fermentations (Castilho L., et al. (2000) Biochemical Engineering Journal, 4: 239-247; Jenkins N. E., et al. (1998) Biocontrol News and Information, 19: 21N-31N; Papagianni M., et al. (2001) Food Technology and Biotechnology, 39: 319-326; Viniegra-Gonzalez G., et al. (2002) Biochemical Engineering Journal, 3643: 1-11). The technique actually seeks to take advantage of the intrinsic characteristics of solid-substrate fermentation, in the easiest way which is the surface culture, for the biotransformation of ferulic acid into vanillin. In the following Table, some numeric data about submerged culture processes in comparison with our technique are shown;

| Indicators | Submerged bioconversion | Surface bioconversion |
|---|---|---|
| Specific growth rate μ (h$^{-1}$) | 0.19 | 0.71 |
| Productivity (moles h$^{-1}$) | 6.85 × 10$^{-4}$ | 12.18 × 10$^{-4}$ |
| Selectivity | Medium | High |
| Molar yield | 50-70% | 70-85% |
| Immobilized biomass | Low yields | High yields |
| Purification processes | Less favored | Favored |
| Operational expenses | Bigger | Smaller |
| Investment expenses | Bigger | Smaller |

This Table, shows the multiple advantages of our process which are: 1) a higher growth rate of microorganisms; 2) a bigger yield from the process; 3) a high level of selectivity in the biotransformation process since vanillin is almost the only resulting product; 4) immobilized actinomycetes allow the system to act as a unique system of biocatalysis right after the immobilization process; 5) the process is more economical since the operational costs pertaining to the raw materials of the culture medium, as well as the cost of utilities are reduced to the same amount of times as the amount of biotransformation cycles (3 to 15 cycles) as compared to a submerged batch of cultures; 6) the technical complexity of the described process is minimal, thus, there is a reduction in the investment expenses for facilities and for equipment than that which is required for submerged culture processes; 7) the recovery and purification processes are much more favorable because the resulting biotransformation solution contains vanillin as almost the only product due to the highly selective process. It also doesn't contain inorganic salts or other residual nutrients of the culture broth, as occurs in submerged culture processes; 8) also the characteristics of the system favor transfer processes of biomass, mainly oxygen, and therefore our system is of high performance as described in the previous points. Other mentioned patents (WO-9634971) reveal that a submerged process with immobilized actinomycetes in alginate pellets have lower yields than those obtained with immobilized actinomycetes by surface culture.

Therefore, the obvious metabolic and physiological differences between the microorganisms cultivated by submerged fermentation or by solid-state fermentation, and the intrinsic advantages of this last system during the biotransformation process and moreover, the operational characteristics for the biotransformation, justifies the fact that the process described in this technique is considered to be different from any other technique described in submerged culture.

Also, it is important to distinguish the novo synthesis from biotransformation or bioconversion processes. In the first case, an enzyme or a metabolite is formed from a very simple molecule, like glucose, through very complex biochemical pathways, while bioconversion involves the transformation of precursors (preformed molecules) into a product in just a few steps through biocatalysis. Vanillin is not a product of the natural metabolism of the actinomycete that was used, therefore it cannot be considered as a metabolite. Vanillin is the result of a process of disintoxication of the microorganism in order to reduce the concentration of ferulic acid which is toxic, thus transforming this compound into a less toxic product like vanillin. Therefore, other systems described for the novo synthesis that use the surface culture in absorbent-non-fermentable-compressible cubes and/or differently shaped support systems, like the one described in the Mexican patent MX-178723, have different purposes from those described by this technique. One of them is to provide a chemically defined culture media that guarantees the homogeneity of the yields and a second one is to improve the recovery of the products (metabolites or enzymes) since this task is very hard with the conventional substrates (rice, rice bran, wheat bran, etc.) employed in solid-substrate fermentations. The purpose of our technique is to immobilize an actinomycete in an effective solid support structure so that the system acts as a pure biocatalysis system. The immobilization is possible thanks to the mycelial growth that the actinomycetes develop and that allows them to adhere inside the solid support structure (FIG. 1). Also, its characteristics allow for the draining of the bioconversion solution and to later feed a fresh solution of ferulic acid without causing significant damage to the actinomycetal lattice, repeating the process in several biocatalytic cycles, a fundamental advantage of our technique. Most would have assumed that the lack of nutrients and the constant exposure of the actinomycetes to the toxic effects of ferulic acid would cause a rapid loss of cellular viability and consequently a loss of catalytic capacity. But our method reveals that the biocatalysis did occur and the process can be repeated between 3 to 15 times when ideal conditions exist.

EXAMPLES OF THE UTILIZATION OF THE INVENTION

The invention will now be described with respect to the following examples, which are solely for the purpose of showing how to carry out the implementation of the basic elements of the invention. The following examples do not intend to be an exhaustive representation of the invention, or to limit its scope.

Example 1

Erlenmeyer flasks of 250 ml containing 1 g of polyurethane foam chopped in small cubes were added with 20 ml of a culture broth previously inoculated with 0.8 ml of preculture of *Streptomyces setonii* ATCC 39116, grown in a flask under agitation 190 min$^{-1}$, incubated at 99° F., for 20 hours. The culture broth contained 10 gl$^{-1}$ of glucose, 4 gl$^{-1}$ of yeast extract, 40 gl$^{-1}$ of Na$_2$HPO$_4$, 1 gl$^{-1}$ of KH$_2$PO$_4$, 0.2 gl$^{-1}$ of MgSO$_4$ 7H$_2$O, 0.2 gl$^{-1}$ of NaCl and 0.05 gl$^{-1}$ of CaCl$_2$.H$_2$O, with a pH of 7.2. The surface culture in the flasks was kept at 99° F. for 18 hours, and after which glucose was depleted. After this period, the polyurethane foam cubes were squeezed within a syringe in order to drain the residual culture broth. In order to start the biotransformation, the polyurethane foam cubes containing the immobilized biomass were again placed in the flasks and added with 20 ml of a solution of 10 gl$^{-1}$ of ferulic acid at pH 7.2. The biotransformation was developed at 99° F. for 20 h after which the foam was again squeezed, draining the biotransformation solution that was recovered with a content of 4.3 gl$^{-1}$ of vanillin, 0.7 gl$^{-1}$ of ferulic acid, 0.12 gl$^{-1}$ of vanillic acid, 0.09 g of vanillic alcohol and traces of guaiacol. The calculated conversion molar yield of vanillin was 60%. The foam cubes containing the immobilized microorganisms were returned to the flasks, added again with 20 ml of a fresh solution of 10 gl$^{-1}$ of ferulic acid, maintaining the flasks at 99° F. for a period of 24 hours. The recovered biotransformation solution had a content of 6.1 $gl^{-1}$ of vanillin, 0.39 $gl^{-1}$ of ferulic acid, 0.06 $gl^{-1}$ of vanillic acid, 0.04 $gl^{-1}$ of vanillic alcohol and traces of guaiacol. The biotransformation yield was of 81%. Additionally, 3 biotransformation cycles were developed at the same temperature conditions and for the same amount of time and obtaining similar results to the previous ones. During the 5 biotransformation cycles approximately 90 ml of biotransformation solution per flask were collected.

Example 2

Figure 4:
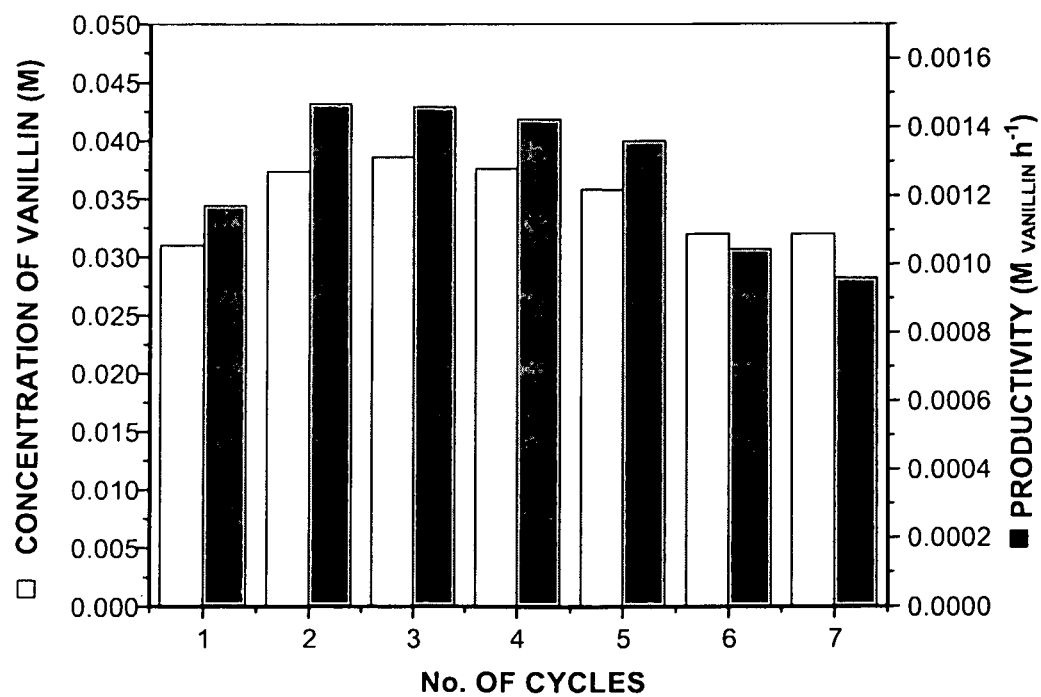
FIG. 4 is a bar graph showing the seven cycles of biocatalysis with the concentration of vanillin reached during such cycles of biotransformation and the volumetric productivity in each one of them.

Covered trays of 12 l, containing 25 g of polyurethane foam cubes were added with 500 ml of culture broth previously inoculated with 20 ml of a preculture of *Streptomyces setonii* ATCC 39116, grown in a flask under agitation at 190 $min^{-1}$, incubated at 99° F. for 20 h. The culture broth contained 15 $gl^{-1}$ of glucose, 6 $gl^{-1}$ of yeast extract, 4 $gl^{-1}$ of $Na_2HPO_4$, 1 $gl^{-1}$ of $KH_2PO_4$, 0.2 $gl^{-1}$ of $MgSO_4$ $7H_2O$, 0.2 $gl^{-1}$ of NaCl and 0.05 $gl^{-1}$ of $CaCl_2H_2O$, with a pH of 7.2. The surface culture in the trays was developed at 99° F. for a period of 24 hours, after which the amount of glucose was depleted. After this period of time, the polyurethane foam cubes were squeezed inside the trays in order to remove the residual culture broth. Then, 500 ml of a solution of 10 $gl^{-1}$ of ferulic acid with a pH of 7.2 was added. The biotransformation was developed at 99° F. for a period of 24 hours, and then the biotransformation solution containing 4.71 $gl^{-1}$ of vanillin, 0.63 $gl^{-1}$ of ferulic acid, 0.07 $gl^{-1}$ of vanillic acid, 0.06 g of vanillic alcohol and traces of guaiacol was collected in a manner similar to the previous example. Once converted, the vanillin molar yield was calculated at 64%. In a second cycle, 500 ml of a fresh solution of 10 $gl^{-1}$ of ferulic acid were added again, maintaining the trays at 99° F. during a period of 24 hours. The recovered biotransformation solution had a content of 5.87 $gl^{-1}$ of vanillin, 0.24 $gl^{-1}$ of ferulic acid, 0.14 $gl^{-1}$ of vanillic acid, 0.10 $gl^{-1}$ of vanillic alcohol and 0.04 g of guaiacol. The conversion yield was of 77%. Additionally the biotransformation was repeated for 5 cycles under the same temperature conditions and during the same time period obtaining similar results to the previous ones. During the 7 biotransformation cycles a total of 3.2 L of solution per tray containing approximately 5.6 $gl^{-1}$ of vanillin were collected. See FIG. 4.

For the recovery and purification of the vanillin, a flask containing the biotransformation solution was added with 100 g of activated charcoal and kept under agitation for 5 hours, after which the supernatant was discarded. The elution was carried out with 100 ml of ethanol 95% (v/v) under agitation for a period of 3 hours. The ethanolic solution was concentrated through evaporation, reducing its volume to 30 ml. Next 30 ml of water were added, and was then allowed to stand for 12 hours, after which the vanillin crystallized.

Example 3

Another method for applying the invention: 150 g of amberlite XAD-4 was used instead of the activated charcoal used in example 2, and carrying out the same steps until the crystallization of the vanillin occurs.

The advantages of the invention with regard to the state of the art the can be summarized with the following points:
The process allows the biotransformation of ferulic acid and the accumulation of vanillin in concentrations that are industrially appealing (of approximately 3 $gl^{-1}$ to approximately 12 $gl^{-1}$). See FIG. 4.

Figure 2:
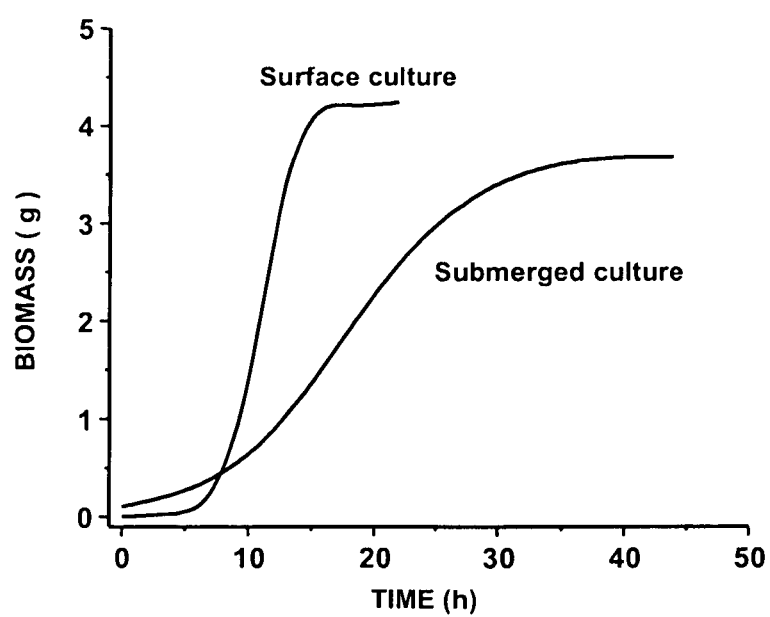
FIG. 2 is a graph which compares the growth profile of *Streptomyces setonii* in a submerged culture to the growth profile of *Streptomyces setonii* in a surface culture in polyurethane foam.
Figure 3:
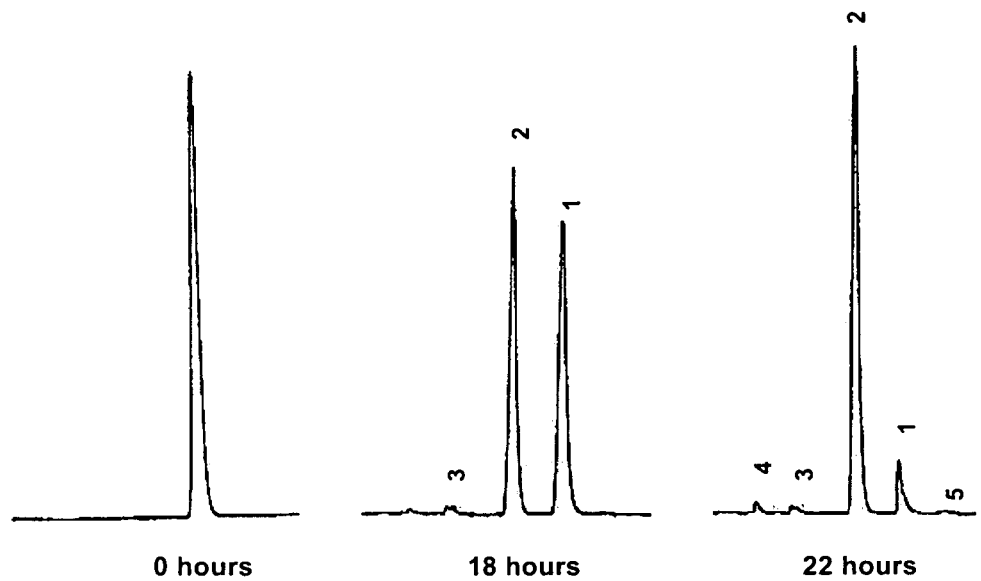
FIG. 3 is a graph showing the course of the biotransformation process, based on the use of high performance liquid chromatography (HPLC); (a) when it was initiated, (b) 18 hours later, and (c) 22 hours later when the bioconversion has to be stopped, where (1) is ferulic acid, (2) vanillin, (3) vanillic alcohol; (4) vanillic acid; and (5) guaiacol.

Thanks to the intrinsic advantages of the surface culture, the specific growth rate ($\mu$=0.71 $h^{-1}$) of the *Streptomyces setonii* strain ATCC 39116 is increased up to three times in comparison to its growth in a submerged culture ($\mu$=0.19 $h^{-1}$), reducing the time for the development of the microorganism. See FIG. 2.

When compared to the submerged processes, the conversion process by surface culture is much more selective since vanillin is almost the only product of the biotransformation.

The system used allows the adherence of the microorganisms to an effective solid support system; thus it is possible to reuse them for more biotransformation processes (cycles) by feeding them with a fresh solution of ferulic acid.

The operational expenses associated with the raw materials of the culture media, as well as the auxiliary utilities are reduced by same number of times as the quantity of biotransformation cycles (3 to 15 cycles), in comparison with the submerged batch cultures.

The process of applying this invention is more economical, because the cost of investing in facilities and equipment is less than what is required for submerged culture processes.

The recovery and purification processes are highly favorable because the resulting solutions of the biotransformation contain vanillin as virtually the only product due to the high degree of selectivity of the process. It also doesn't contain inorganic salts or other residual nutrients from the culture broth as occurs in the processes that use submerged systems.

In general the industrial scaling of the processes by surface culture or solid-substrate culture is simpler than the processes in submerged culture.

Based on the previously described accomplishments, we believe that we have created a sate of the art technique. Therefore, we are making the following claims with respect to our invention.

We claim:

1. A cyclic process to produce vanillin from ferulic acid or a salt thereof, comprising:
    (a) preparing a solid support system comprising one or more pieces of an inert, porous, absorbent and compressible material, having a bed height between 1 cm and 10 cm in a container and thereby being configured for aeration and promoting mycelial growth on a surface area of between 3000 $cm^2$ per gram of the solid support and 4000 $cm^2$ per gram of the solid support;
    (b) impregnating the solid support system with a liquid culture broth inoculated with *Streptomyces setonii* strain ATCC39116;
    (c) Growing *Streptomyces setonii* strain ATCC39116b1945 at a maximum specific growth rate of 0.71 $h^{-1}$ on the surface culture promoted by the solid support system;
    (d) Draining the exhausted culture broth to produce a drained-immobilized surface culture from *Streptomyces setonii* strain ATCC39116;
    (e) Impregnating the drained-immobilized surface culture from *Streptomyces setonii* strain ATCC39116 with a solution of ferulic acid or a salt thereof;
    (f) incubating the solution and the immobilized surface culture comprising *Streptomyces setonii* strain ATCC39116;

(g) producing vanillin from ferulic acid by the surface culture at a rate of $12.18 \times 10^{-4}$ moles $h^{-1}$;

(h) collecting the solution comprising vanillin by force from the solid support system; and (i) repeating steps (e)-(h), said steps (e)-(h) are repeated between 3 and 15 times, said surface culture yielding a percentage conversion of ferulic acid or a salt thereof to vanillin of at least 70%.

2. The process of claim 1, wherein step (e) comprises the solution of ferulic acid or a salt thereof in a concentration (w/v) ranging from 5 g/l to 30 g/l.

3. The process of claim 1, wherein step (e) comprises: 1) adding the solution of ferulic acid or a salt thereof in a volume of 5 ml per gram of solid support to 50 ml per gram of solid support; and (2) forming thin interstitial films that allow aeration and to avoid the downward seepage of the absorbed liquid due to gravity.

4. The process of claim 1, wherein step (e) comprises the solution of ferulic acid or a salt thereof having a pH between 7 and 9.

5. The process of claim 1, wherein the solid support structure comprises a foam having a density between 0.005 g/mL and 0.070 g/mL.

6. The process of claim 1, wherein step (f) comprises incubating for between 7 hrs and 48 hrs at a temperature of 98° F.

7. The process of claim 1, wherein step (h) comprises collecting the solution comprising vanillin by force by at least one of compression, centrifugation, vacuum, vacuum filtration, and squeezing.

8. The process of claim 1, wherein step (b), comprises the preparation of an inoculum by submerged culture of the *Streptomyces setonii* strain ATCC39116 in an aliquot of the liquid broth shaking for 190 $min^{-1}$ and a temperature of 99° F. for 20 hrs.

9. The process of claim 1, wherein step (b) comprises adding the inoculum to the liquid culture broth in a volume of 3% to 6% (v/v), of the culture broth.

10. The process of claim 1, wherein step (b) comprises a liquid culture broth and concentration chosen from:

(1) glucose or maltose having a concentration ranging between 8 g/l and 40 g/l;

(2) yeast extract sources having a concentration ranging between 1 g/l and 15 g/l; and (3) a magnesium source.

11. The process of claim 1, wherein step (b) comprises:

(1) adding the inoculated culture broth in a volume ranging from 5 ml per gram of solid support to 50 ml per gram of solid support; and (2) forming thin interstitial films that allow aeration and to avoid the downward seepage of the absorbed liquid due to gravity.

12. The process of claim 1, wherein step (c) comprises incubating the inoculated culture thin interstitial films for between 6 hrs and 35 hrs, at a temperature between 86° F. and 113° F. for growing and immobilizing *Streptomyces setonii* strain ATCC39116.

13. The process of claim 1, wherein step (d) comprises eliminating the exhausted culture broth by at least one of compression, centrifugation, vacuum, vacuum filtration, and squeezing.

* * * * *